United States Patent [19]

Gutheil

[11] Patent Number: 5,574,017

[45] Date of Patent: Nov. 12, 1996

[54] ANTIBACTERIAL AGENTS

[76] Inventor: William G. Gutheil, 7 Ocean View Dr., Apt. 710, Boston, Mass. 02125

[21] Appl. No.: 270,818

[22] Filed: Jul. 5, 1994

[51] Int. Cl.$^6$ .......................... A61K 38/05; A61K 38/04; A61K 31/69

[52] U.S. Cl. .................... 514/19; 514/18; 514/64; 530/331; 548/110; 560/10; 560/29; 560/37; 560/45; 560/80; 560/100; 562/445; 562/448; 562/556; 564/8

[58] Field of Search ............................... 530/331; 514/18, 514/19, 64; 548/110; 560/10, 18, 29, 37, 45, 80, 100, 110; 564/8; 562/445, 448, 558

[56] References Cited

U.S. PATENT DOCUMENTS

| | | | |
|---|---|---|---|
| 4,424,207 | 1/1984 | Szelke et al. | 514/14 |
| 4,963,655 | 10/1990 | Kinder et al. | 530/331 |
| 5,055,451 | 10/1991 | Krantz et al. | 514/19 |
| 5,166,321 | 11/1992 | Lai et al. | 530/324 |
| 5,196,515 | 3/1993 | Lever et al. | 530/363 |
| 5,288,707 | 2/1994 | Metternich | 514/19 |

OTHER PUBLICATIONS

Fisher et al, 1980, Biochemistry 19:2895–2901.
Sutherland, 1990 J. Reproduct. Med. 35:307–312.
Sutton et al, 1987, Biochemical J. 248:181–188.
Iaconis & Sanders, 1990, Antimicrob. Agents Chemother. 34:44–51.
Gordon et al, J. of Medic. Chemistry, 37, 1385–1401, 1994.
Dougherty et al, 1981, Antimicrob. Agents Chemother. (1), 109–14.
Green et al, J. of Biol. Chem. 286(4), pp. 1923–1928 (1981).

*Primary Examiner*—Howard E. Schain
*Attorney, Agent, or Firm*—Lahive & Cockfield; Matthew P. Vincent; Giulio A. DeConti, Jr.

[57] ABSTRACT

The present invention provides methods and pharmaceutical preparations for inhibiting the growth of bacterial microorganisms.

21 Claims, 3 Drawing Sheets

ANTIBACTERIAL AGENTS

BACKGROUND OF THE INVENTION

The penicillin binding proteins (PBPs) are ubiquitous bacterial enzymes involved in cell wall biosynthesis (reviewed in Waxman et al., 1983 Annual Review of Biochemistry 58:825–869; Georgopapadkou et al., 1983 Handbook of Experimental Pharmacology 67:1–77; and Ghuysen, 1991 Annual Review of Microbiology 45:37–67). In *Staphylococcus aureus* these enzymes catalyze the general reaction shown in FIG. 1 which introduces cross links into the cell wall necessary for its structural integrity. Variations on this theme are known in other bacteria (reviewed in Schleifer et al., 1972 Bacteriology Review 36:407–477). The active site serine involved in the acyl transfer reaction is the target of the β-lactam antibiotics. Most bacteria posses a number of variants of this enzyme; *E. coli* has seven known variants labeled 1A, 1B, and 2–6. The different PBPs have different propensities towards the transpeptidation cross linking reaction shown in FIG. 1 and hydrolysis of the acyl enzyme intermediate in a proteolytic-like reaction. Those enzymes for which hydrolysis is the predominant path are also known as the (DD)-carboxypeptidases. The β-lactam antibiotics inhibit the PBPs by acting as substrate analogs and forming an acyl enzyme intermediate. This acyl enzyme intermediate is resistant to subsequent hydrolysis and ties up the enzyme in a relatively long lived inactive form. This is the mechanism by which the β-lactam antibiotics inhibit bacterial cell wall biosynthesis.

Bacteria have responded to the widespread use of β-lactam antibiotics by evolving a class of β-lactam hydrolyzing enzymes known as β-lactamases. These enzymes are one of the sources of drug resistance now being observed in a number of bacterial diseases including tuberculosis, malaria, pneumonia, meningitis, dysentery, bacteriemia, and various venereal diseases. A special issue of Science (Science, Aug. 21, 1992) has been devoted to this serious public health issue. The serine β-lactamases operate on β-lactams in much the same fashion as do the PBPs except that the hydrolysis step to release the bound inhibitor is relatively fast. This allows the β-lactamases to hydrolyze a susceptible β-lactam antibiotic and render it inactive (Fisher et al., 1980 Biochemistry 19:2895–2901). A considerable amount of research has now been devoted to finding compounds which can inhibit β-lactamases (reviewed in Sutherland, R., 1990 J. Reproduct. Med. 35:307–312). Most such efforts have been directed towards inhibiting β-lactamases with β-lactam compounds, such as clavulanic acid, so that the traditional β-lactam antibiotics can survive long enough to kill the cells. Clavulanic acid is a β-lactam serine β-lactamase inhibitor currently being used in conjunction with β-lactam antibiotics to treat resistant bacterial infections. The rapid development of resistance to this type of therapy illustrates that this strategy can only provide a temporary solution to β-lactam resistance. The β-lactam antibiotics, while bearing some similarity to the -(D)-Ala-(D)-Ala physiological substrate of the PBPs (Tipper & Strominger, 1965 Proc. Natl. Acad. Sci. USA 54:1133–1141), are sufficiently different in structure that it has not been difficult for β-lactamases to evolve which discriminate between the β-lactams and the physiological substrate for the PBPs. Given the evolutionary mobility of the β-lactamases, highlighted by the evolution of zinc β-lactamases (Sabath & Abraham, 1966 Biochem. J. 98:11c–13c; Saino et al., 1982 Antimicrob. Agents Chemother. 22:564–570; Sutton et al., 1987 Antimicrob. J 248:181–188; Iaconis & Sanders, 1990 Antimicrob. Agents Chemother. 34:44–51), the prospects for keeping ahead of the evolution of drug resistant bacteria with β-lactamase inhibitors appear dim.

SUMMARY OF THE INVENTION

There exists a need to provide alternative and improved agents for the treatment of bacterial infections particularly for the treatment of infections caused by, for example, resistant strains of bacteria, e.g. penicillin-resistant strains, as well for the decontamination of objects bearing such organisms, e.g. non-living matter, e.g. hospital equipment, walls of operating rooms and the like.

In general, the present invention provides a method and pharmaceutical preparations for inhibiting the growth of bacterial microorganisms, such as in the treatment of Staphylococcus infections, Streptococcus infections, Enterobacteriaceae infections, Enterococcus infections, Mycobacterium infections, Neisseria infections, Pseudomonas infections, Shigella infections, Escherichia infections, Bacillus infections, Micrococcus infections, Arthrobacter infections, or Peptostreptococcus infections. For instance, the compounds of the present invention are particularly useful in the treatment of infections caused by penicillin-resistant strains of bacteria, e.g. penicillin-resistant strains of *Staphylococcus aureus* (*Micrococcus pyogenes* var. *aureus*). In preferred embodiments, the present invention can be used to inhibit bacterial infections caused by, for example, *S. aureus, S. epidermidis, S. pneumoniae, S. sanguis, H. influenza, N. gonorrhoeae, N. meningitidis, E. coli, P. aeruginosa, E. cloacae, S. marcescens, K. pneumoniae, K. oxytoca, Enterococci, P. aeruginosa, Moraxella, S. marcescens,* Bacteroides, Acinebacter, Salmonella, Shigella, or Haemophilus.

The invention, as described herein, is directed to the use of inhibitors of penicillin binding proteins as antibacterial agents. The PBPs are enzymes which catalyze the bacterial cell wall cross linking reaction via a serine acyl enzyme intermediate. Specifically proposed as antibacterial agents are classes of compounds which can facilly interconvert between trigonal and tetrahedral forms in a fashion which allows the compounds to bind rapidly and tightly to the PBPs. As described herein suitably designed peptide mimetics and analogs possesing in place of the sicile bond of the normal peptide-(D)-Ala-X substrate a boronic acid, aldehyde, ketone, α-haloketone, α-difluoromethylketone, α-trifluoromethylketone, or α-alkoxymethylketone are useful for such applications. In general it is expected that the (D)-Ala analog in the $P_1$ position will be the prefered inhibitor, but the (L) and (DL) compounds are also possible antibacterial agents. The use of analogs of amino acids other than Ala in the $P_1$ position, and a wide variety of other modifications in other areas of these compounds, offers the possibility of affecting the potency, specificity, solubility, bioavailability, stability, toxicity, and other physical properties to suit specific purposes.

DETAILED DESCRIPTION OF THE INVENTION

Figure 1:
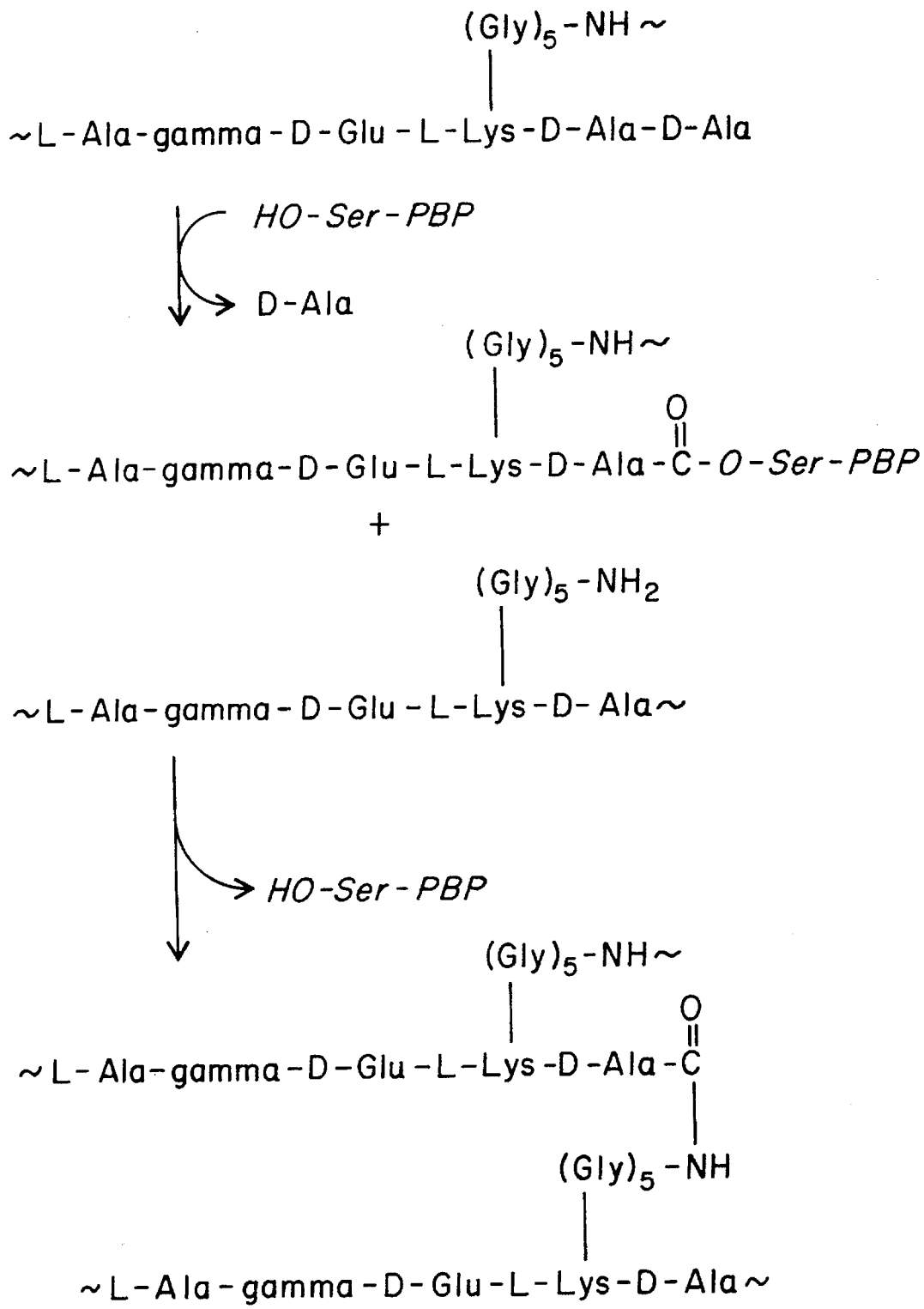
FIG. 1 illustrates the reaction catalyzed by the PBP of *Staphylococcus aureus* in the synthesis of its cell wall.

In the last several years, the frequency and spectrum of antimicrobial-resistant infections have increased in both the hospital and the community. Certain infections that are essentially untreatable have begun to occur as epidemics both in the developing world and in institutional settings in the United States. Antimicrobial resistance is resulting in increased morbidity, mortality, and health-care costs. As described above, a considerable amount of effort has been devoted to finding inhibitors of β-lactamases with the hopes that such compounds will prove effective in the treatment of, for example, penicillin-resistant strains. However, the prospect of keeping ahead of the evolution of drug resistant bacteria with such inhibitors appears dim. In contrast, Applicant has realized that the penicillin binding proteins (PBPs) are physiologically constrained by the requirements for cell wall synthesis and can not, therefore, evolve as rapidly to circumvent inhibitors of PBP activity as can the β-lactamases.

Accordingly, the present invention makes available a method for inhibiting bacterial growth by contacting bacterial cells with compounds represented by the general formula;

$$R_1-N-\underset{W}{\underset{|}{C}}\genfrac{}{}{0pt}{}{R_2\;\;R_3}{|\;\;|}-R_4$$

wherein

W represents $BY_1Y_2$, or $C(=O)R_5$ $R_1$ represents a C-terminally linked amino acid residue or amino acid analog, or a C-terminally linked peptide or peptide analog, or $$R_6-\overset{O}{\overset{\|}{C}}-,\; R_6-\overset{S}{\overset{\|}{C}}-,\; R_6-\overset{O}{\underset{\underset{O}{\|}}{\overset{\|}{S}}}-;$$

$R_2$ represents hydrogen, an alkyl, an alkenyl, an alkynyl, —(CH$_2$)m-R$_7$, —(CH$_2$)m-OH, —(CH$_2$)m-O-alkyl, —(CH$_2$)m-O-alkenyl, —(CH$_2$)m-O-alkynyl, —(CH$_2$)m-O-C(=O)-alkyl, —(CH$_2$)m-O-C(=O)-alkenyl, —(CH$_2$)m-O-C(=O)-alkynyl -(CH$_2$)m-O-C(=O)-(CH$_2$)m-R$_7$;

$R_3$ and $R_4$ each represent hydrogen, a alkyl, a alkenyl, a alkynyl, —(CH$_2$)m-R$_7$, —(CH$_2$)n-OH, —(CH$_2$)n-O-alkyl, —(CH$_2$)n-O-alkenyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, an α-carbon linked side chain of an amino acid or an amino acid analog, $$-(CH_2)_n-N\genfrac{}{}{0pt}{}{R_8}{R_9},\; -(CH_2)_n-\overset{O}{\overset{\|}{C}}-N\genfrac{}{}{0pt}{}{R_8}{R_9},$$

$$-(CH_2)_n-NH_2-\overset{NH_2}{\overset{\|}{C}}-NH_2,\; -(CH_2)_n-\overset{O}{\overset{\|}{C}}-O-R_7$$

$$-(CH_2)_n-\overset{O}{\overset{\|}{C}}-\text{alkyl},\; -(CH_2)_n-\overset{O}{\overset{\|}{C}}-\text{alkenyl},\; -(CH_2)_n-\overset{O}{\overset{\|}{C}}-\text{alkynyl},$$

or $$-(CH_2)_n-\overset{O}{\overset{\|}{C}}-(CH_2)_{\overline{m}}-R_7$$

$R_2$ and $R_3$ taken together can complete a ring having from 4 to 8 atoms in the ring structure, or, provided $R_2$ and $R_3$ are not taken together forming a ring, $R_3$ and $R_4$ taken together can complete a ring having from 3 to 8 atoms in the ring structure, $Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure, $R_5$ represents H, an alkyl, an alkenyl, an alkynyl, —(CH$_2$)m-R$_7$, —(CH$_2$)n-OH, —(CH$_2$)m-O-alkyl, —(CH$_2$)n-O-alkenyl, —(CH$_2$)n-O-alkynyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, —CH$_2$O-R$_{10}$, $R_6$ represents hydrogen, a halogen, a alkyl, a alkenyl, a alkynyl, an aryl, —(CH$_2$)$_m$-R$_7$, —(CH$_2$)$_m$-OH, —(CH$_2$)$_m$-O-alkyl, —(CH$_2$)$_m$-O-alkenyl, —(CH$_2$)$_m$-O-alkynyl, —(CH$_2$)$_m$-O-(CH$_2$)$_m$-R$_7$, —(CH$_2$)$_m$-SH, —(CH$_2$)$_m$-S-alkyl, —(CH$_2$)$_m$-S-alkenyl, —(CH$_2$)$_m$-S-alkynyl, —(CH$_2$)$_m$-S-(CH$_2$)$_m$-R$_7$, $$-(CH_2)_m-N\genfrac{}{}{0pt}{}{R_8}{R_9},\; -(CH_2)_n-\overset{O}{\overset{\|}{C}}-N\genfrac{}{}{0pt}{}{R_8}{R_9},$$

$$-(CH_2)_n-NH_2-\overset{NH_2}{\overset{\|}{C}}-NH_2,\; -(CH_2)_n-\overset{O}{\overset{\|}{C}}-O-R_7$$

$$-(CH_2)_n-\overset{O}{\overset{\|}{C}}-\text{alkyl},\; -(CH_2)_n-\overset{O}{\overset{\|}{C}}-\text{alkenyl},\; -(CH_2)_n-\overset{O}{\overset{\|}{C}}-\text{alkynyl},$$

or $$-(CH_2)_n-\overset{O}{\overset{\|}{C}}-(CH_2)_{\overline{m}}-R_7$$

$R_7$ represents an aryl, a cycloalkyl, a cycloalkenyl, or a heterocycle;

$R_8$ and $R_9$ each independently represent hydrogen, alkyl, alkenyl, —(CH$_2$)$_m$-R$_7$, —C(=O)-alkyl, —C(=O)-alkenyl, —C(=O)-alkynyl, —C(=O)-(CH$_2$)$_m$-R$_7$, or $R_8$ and $R_9$ taken together with the N atom to which they are attached complete a heterocyclic ring having from 4 to 8 atoms in the ring structure;

$R_{10}$ represents represents a C-terminally linked amino acid residue or amino acid analog, or a C-terminally linked peptide or peptide analog, $$R_6-\overset{O}{\overset{\|}{C}}-,\; R_6-\overset{S}{\overset{\|}{C}}-,\; \text{or}\; R_6-\underset{\underset{O}{\|}}{\overset{\overset{O}{\|}}{S}}-;$$

m is zero or an integer in the range of 1 to 8; and n is an integer in the range of 1 to 8.

Also deemed as equivalents are any compounds which can be hydrolytically converted into any of the aforementioned compounds including boronic acid esters and halides, and carbonyl equivalents including acetals, hemiacetals, ketals, and hemiketals, and cyclic dipeptide analogs.

In preferred embodiments, the subject antibacterial agents are boronic acid analogs of an amino acid. For example, the present invention contemplates the use of boro-alanine, especially (D)-boro-alanine, for inhibiting bacterial infections. Exemplary boronic acid derived inhibitors of the present invention are represented by the general formula:

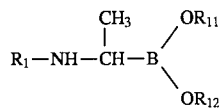

wherein $R_1$ represents a C-terminally linked amino acid residue or amino acid analog, or a C-terminally linked peptide or peptide analog, or

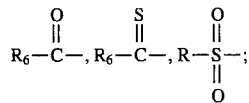

$R_6$ represents hydrogen, a halogen, a alkyl, a alkenyl, a alkynyl, an aryl, —$(CH_2)_m$-$R_7$, —$(CH_2)_m$-OH, —$(CH_2)_m$-O-alkyl, —$(CH_2)_m$-O-alkenyl, —$(CH_2)_m$-O-alkynyl, —$(CH_2)_m$-O-$(CH_2)_m$-$R_7$, —$(CH_2)_m$-SH, —$(CH_2)_m$-S-alkyl, —$(CH_2)_m$-S-alkenyl, —$(CH_2)_m$-S-alkynyl, —$(CH_2)_m$-S-$(CH_2)_m$-$R_7$,

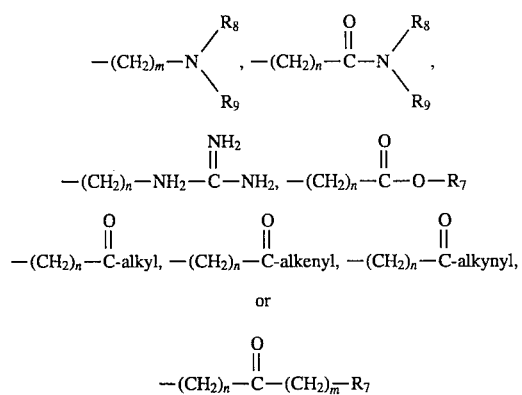

$R_7$ represents an aryl, a cycloalkyl, a cycloalkenyl, or a heterocycle;

$R_8$ and $R_9$ each independently represent hydrogen, alkyl, alkenyl, —$(CH_2)_m$-$R_7$, —C(=O)-alkyl, —C(=O)-alkenyl, —C(=O)-alkynyl, —C(=O)-$(CH_2)_m$-$R_7$, or $R_8$ and $R_9$ taken together with the N atom to which they are attached complete a heterocyclic ring having from 4 to 8 atoms in the ring structure;

$R_{11}$ and $R_{12}$ each independently represent hydrogen, a alkyl, or a pharmaceutically acceptable salt, or $R_{11}$ and $R_{12}$ taken together with the O-B-O atoms to which they are attached complete a heterocyclic ring having from 5 to 8 atoms in the ring structure;

m is zero or an integer in the range of 1 to 8; and n is an integer in the range of 1 to 8.

In other embodiments, the subject antibacterial agents are aldehyde analogs of an amino acid. For example, the present invention contemplates the use of alaninal compounds, especially (D)-alaninal, for inhibiting bacterial infections. Exemplary aldehyde-derived inhibitors of the present invention are represented by the general formula:

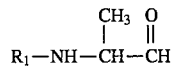

wherein $R_1$ represents a C-terminally linked amino acid residue or amino acid analog, or a C-terminally linked peptide or peptide analog, or

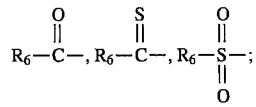

$R_6$ represents hydrogen, a halogen, a alkyl, a alkenyl, a alkynyl, an aryl, —$(CH_2)_m$-$R_7$, —$(CH_2)_m$-OH, —$(CH_2)_m$-O-alkyl, —$(CH_2)_m$-O-alkenyl, —$(CH_2)_m$-O-alkynyl, —$(CH_2)_m$-O-$(CH_2)_m$-$R_7$, —$(CH_2)_m$-SH, —$(CH_2)_m$-S-alkyl, —$(CH_2)_m$-S-alkenyl, —$(CH_2)_m$-S-alkynyl, —$(CH_2)_m$-S-$(CH_2)_m$-$R_7$,

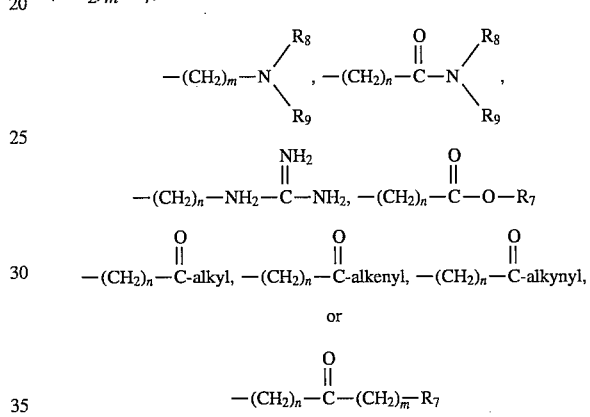

$R_7$ represents an aryl, a cycloalkyl, a cycloalkenyl, or a heterocycle;

$R_8$ and $R_9$ each independently represent hydrogen, alkyl, alkenyl, —$(CH_2)_m$-$R_7$, —C(=O)-alkyl, —C(=O)-alkenyl, —C(=O)-alkynyl, —C(=O)-$(CH_2)_m$-$R_7$, or $R_8$ and $R_9$ taken together with the N atom to which they are attached complete a heterocyclic ring having from 4 to 8 atoms in the ring structure; and m is zero or an integer in the range of 1 to 8; and n is an integer in the range of 1 to 8.

In yet further embodiments, the subject antibacterial agents are halo-methyl ketone analogs of an amino acid. Exemplary inhibitors of this class include compounds represented by the general formula:

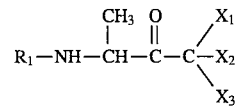

wherein $R_1$ represents a C-terminally linked amino acid residue or amino acid analog, or a C-terminally linked peptide or peptide analog, or

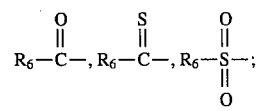

$R_6$ represents hydrogen, a halogen, a alkyl, a alkenyl, a alkynyl, an aryl, —$(CH_2)_m$-$R_7$, —$(CH_2)_m$-OH, —$(CH_2)_m$-

O-alkyl, —(CH$_2$)$_m$-O-alkenyl, —(CH$_2$)$_m$-O-alkynyl, —(CH$_2$)$_m$-O-(CH$_2$)$_m$-R$_7$, —(CH$_2$)$_m$-SH, —(CH$_2$)$_m$-S-alkyl, —(CH$_2$)$_m$-S-alkenyl, —(CH$_2$)$_m$-S-alkynyl, —(CH$_2$)$_m$-S-(CH$_2$)$_m$-R$_7$,

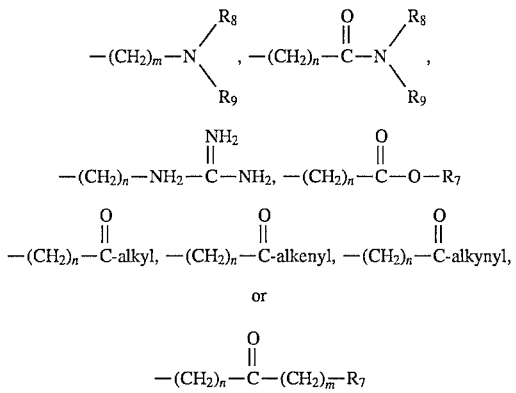

R$_7$ represents an aryl, a cycloalkyl, a cycloalkenyl, or a heterocycle;

R$_8$ and R$_9$ each independently represent hydrogen, alkyl, alkenyl, —(CH$_2$)$_m$-R$_7$, —C(=O)-alkyl, —C(=O)-alkenyl, —C(=O)-alkynyl, —C(=O)-(CH$_2$)$_m$-R$_7$, or R$_8$ and R$_9$ taken together with the N atom to which they are attached complete a heterocyclic ring having from 4 to 8 atoms in the ring structure;

X$_1$, X$_2$ and X$_3$ each represent a hydrogen or a halogen; and m is zero or an integer in the range of 1 to 8; and n is an integer in the range of 1 to 8.

As used herein, the definition of each expression, e.g. alkyl, m, n, etc., when it occurs more than once in any structure, is intended to be independent of its definition elsewhere in the same structure.

In exemplary embodiments, the compounds of the present invention are Ac$_2$-(L)-Lys-(D)-boroAla, Ac$_2$-OMe-meso-DAP-(D)-Alaninal, and Ac$_2$-(L)-Lys-(D)-Ala trifluoro-methyl ketone.

In illustrative embodiments, R$_1$ can be selected from a group consisting of Ac$_2$-(L)-Lys, Ac$_2$-OMe-diaminopimelic acid, -(D)-γ-Glu-(L)-Lysine. For instance, given the known substrate for the *Staphylococcus aureus* PBP, preferred inhibitors have the general formula Ac$_2$-(L)-Lys-(D)-CH(CH$_3$)-W. Likewise, many other classes of bacteria, including *E. coli*, utilize diaminopimelic acid (DAP) containing precursors in place of lysine in their cell wall biosynthesis. Thus, other preferred inhibitors of the present invention include (Ac$_2$)(MeO)-DAP-CH(CH$_3$)-W, with W as defined above. Great variation in the peptidoglycan cell wall has been observed (reviewed in Schleifer et al., 1972 Bacteriology Review 36:407–477), and it can therefore be expected that certain of the subject inhibitors can be designed to provide specificity towards particular species of bacteria.

The term "alkyl" is recognized in the art and refers to saturated aliphatic groups having one to ten carbon atoms, including straight-chain alkyl groups, branched-chain alkyl groups, cycloalkyl (alicyclic) groups, alkyl substituted cycloalkyl groups, and cycloalkyl substituted alkyl groups. Such hydrocarbon moieties may be substituted on one or more carbons with, for example, a halogen, a hydroxyl, a thiol, an amino, or a nitro group. In the instance of the cycloalkyls, such substituents can further comprise an alkyl, an alkenyl, an alkoxy, an alkylthio, an alkylamino, an alkylcarboxyl, a nitro, a hydroxyl, —CF$_3$, —CN, or the like.

Unless the number of carbons is otherwise specified, "lower alkyl" as used herein means an alkyl group, as defined above, but having from one to six carbon atoms, rather than from one to ten carbon atoms. Likewise, "lower alkenyl" and "lower alkynyl" have similar chain lengths.

Representative of such alkyl groups are methyl, ethyl, n-propyl, isopropyl, 2-chloropropyl, n-butyl, sec-butyl, 2-aminobutyl, isobutyl, tert-butyl, 3-thiopentyl, and the like. Other exemplary "alkyls" inlcude CH$_2$Cl, CH$_2$F, CHF$_2$, and CF$_3$. As used herein, the term "amino" means —NH$_2$; the term "nitro" means —NO$_2$; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. The term "alkylthio" refers to an alkyl group, as defined above, having a sulphydryl group attached thereto. The term "alkylcarboxyl" as used herein means an alkyl group, as defined above, having a carboxyl group attached thereto. The term "alkoxy" as used herein means an alkyl group, as defined above, having an oxygen atom, attached thereto. Representative alkoxy groups include methoxy, ethoxy, propoxy, tert-butoxy and the like.

The terms "alkenyl" and "alkynyl" refer to unsaturated aliphatic groups analogous to alkyls, but which contain at least one double or triple bond respectively.

The term "aryl" as used herein includes 4-, 5- and 6-membered single-ring aromatic groups which may include from zero to four heteroatoms, for example, benzene, pyrrole, furan, thiophene, imidazole, oxazole, thiazole, triazole, pyrazole, pyrrolidine, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The term "heterocycle" or "heterocyclic group" refers to 4-, 5- and 6- membered single-ring alicyclic groups which include one to four heteroatoms. Heterocyclic groups include pyrrolidine, oxolane, thiolane, imidazole, oxazole, piperidine, piperazine, morphaline. The alicyclic ring can be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The term "heteroatom" as used herein means an atom of any element other than carbon or hydrogen. Preferred heteroatoms are nitrogen, oxygen, sulphur and selenium.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)-CH$_2$CH$_3$ (the side chain of isoleucine), —CH$_2$CH(CH$_3$)$_2$ (the side chain of leucine) or H-(the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid residue further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxyophenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

The phrase "protecting group" as used herein means substituents which protect the reactive functional group from undesirable chemical reactions. Examples of such protecting groups include esters of carboxylic acids and boronic acids, ethers of alcohols and acetals and ketals of aldehydes and ketones. For instancem the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (FMOC).

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The pharmaceutically acceptable salts of the subject compounds include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the subject compound which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject compounds are also readily prepared by conventional procedures such as treating an acid of Formula I with an appropriate amount of a base such as an alkali or alkaline earth methyl hydroxide (e.g. sodium, potassium, lithium, calcium or magnesium) or an organic base such as an amine, piperidine, pyrrolidine, benzylamine and the like, or a quaternary ammonium hydroxide such as tetramethylammonium hydroxide and the like.

Contemplated equivalents of the compounds described above include compounds which otherwise correspond thereto, and which have the same general properties thereof (e.g. the ability to inhibit bacterial cell growth), wherein one or more simple variations of substituents are made which do not adversely affect the efficacy of the compound in inhibiting bacterial cell growth. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

Moreover, the compounds of the present invention, particularly libraries of variants having various representative classes of substituents, can be generated using combinatorial chemistry (see, for example, PCT WO 94/08051) and rapidly screened in high throughput assays in order to identify potential lead compounds for inhibiting the growth of a particular bacterial species. For instance, simple turbidimetric assays (e.g. measuring the $A_{600}$ of a culture) can be used to assess the effects of a compound on a particular bacterial strain.

In another aspect, the present invention provides pharmaceutically acceptable compositions which comprise a therapeutically-effective amount of one or more of the subject PBP inihibitors, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The antibiotic compounds according to the invention may be formulated for administration in any convenient way for use in human or veterinary medicine, by analogy with other antibiotics.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Besides their use as medicaments in human and veterinary therapy, the compounds of the invention can also be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

The phrase "therapeutically-effective amount" as used herein means that amount of a compound, material, or composition comprising a compound of Formula I which is effective for producing some desired therapeutic effect through inhibiting bacterial growth in at least a sub-population of cells in an animal and thereby blocking the biological consequences of that bacterial growth in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

As set out above, certain embodiments of the compounds useful in the present method may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1–19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such ascorbic acid, cysteine hydrochloride, sodium bisulfate, sodium metabisulfite, sodium sulfite and the like; (2) oil- soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically- acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar, calcium carbonate, potato or tapioca starch, alginic acid, certain silicates, and sodium carbonate; (5) solution retarding agents, such as paraffin; (6) absorption accelerators, such as quaternary ammoniuna compounds; (7) wetting agents, such as, for example, cetyl alcohol and glycerol monostearate; (8) absorbents, such as kaolin and bentonitc day; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in articular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of other microorganisms (e.g. not inhibited by the present compounds) may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compound in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The compounds of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration" "administered systemically" "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the infection, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's infection. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The compounds covered in this invention may be administered alone or in combination with other antibacterial agents or in combination with a pharmaceutically acceptable carrier of dilutent. The compounds of the invention may be administered intravenously, intramuscularly, intraperitoneally, subcutaneously, topically, orally, or by other acceptable means. The compounds may be used to treat bacterial infections in mammals (i.e., humans, livestock, and domestic animals), birds, lizards, and any other organism which can tollerate the compounds, and also to inhibit bacterial growth in cell culture. The compounds can also be used for effects related to their antibacterial activity such as for increasing the weight gain of livestock. The compounds can also be used as analytical reagents to determine the concentration of susceptible PBPs in an unkown sample, in combination with enzymatic assays.

The following examples outline general methods for preparing selected members of each of the above specified classes.

Exemplification

The invention now being generally described, it will be more readily understood by reference to the following examples, which are included merely for purposes of illustration of certain aspects and embodiments of the present invention, and are not intended to limit the invention.

EXAMPLE 1

Figure 3:
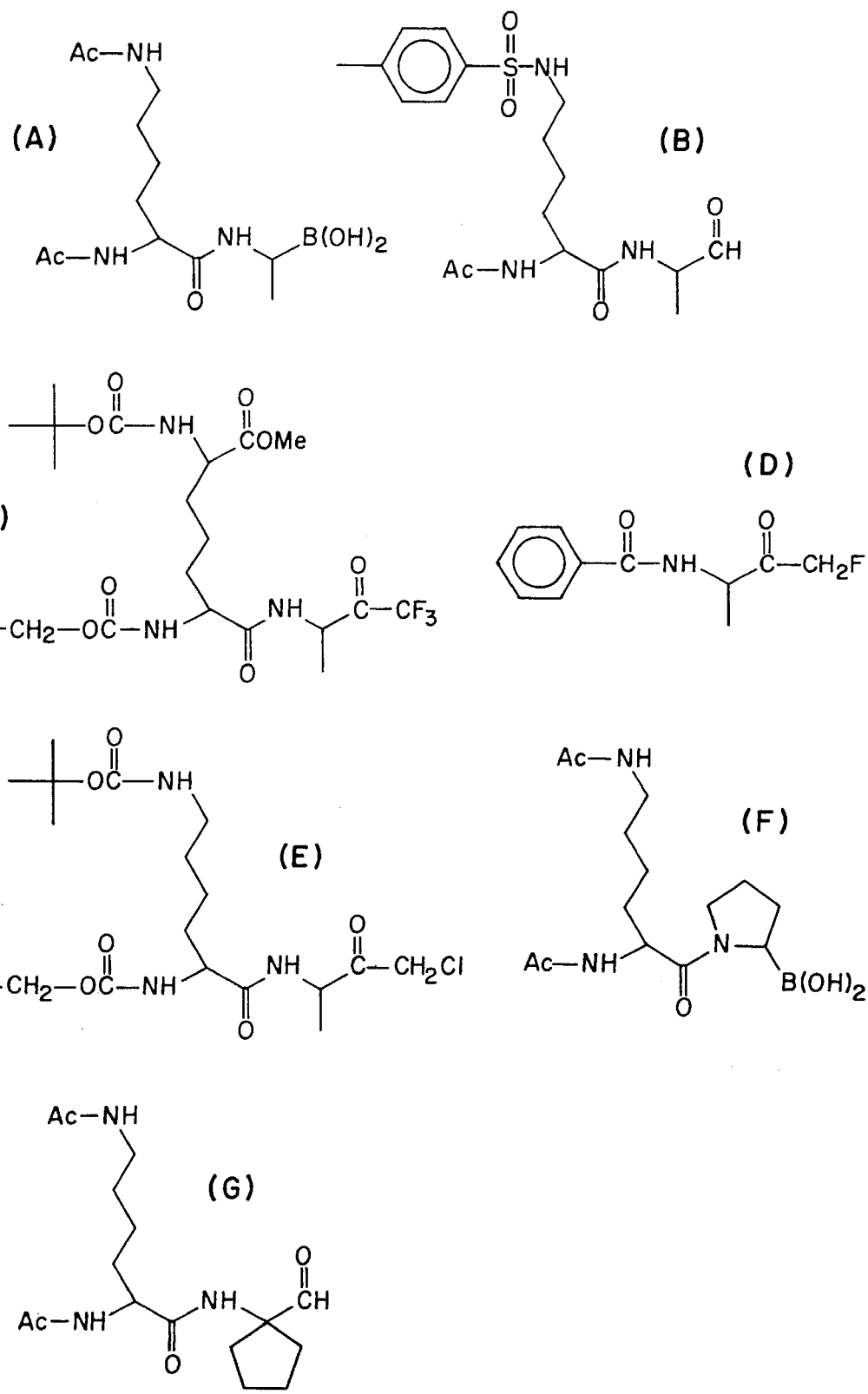
FIG. 3 illustrates the structures of several of the compounds given in the examples.

$Ac_2$-(L)-Lys-(DL)-boroAla (FIG. 3, A)

a. $Ac_2$-(L)-Lys

The following procedure is based upon that of Nieto et al. (Biochem. J. 1971 123 789–803). (L)-Lys (10 mmol) is dissolved in a mixture of dioxane and water (100 ml of 1:1 v:v) and cooled in an ice bath to 0° C. Triethylamine (50 mmol is then added, followed by acetic anhydride (24 mmol). The mixture is kept on ice for 2 hours, boiled for 3 min, and the solvent evaporated to dryness. The residue is redissolved in water and again evaporated to dryness. The un- and mono-acetylated materials and the triethylamine are removed from the di-acetylated material on Dowex-50 (H+ form).

b. (DL)-boroAla (DL)-boroAla is prepared by the method of Duncan et al. (Biochemistry 1989 28:3541–3549). A solution of dichloromethyllithium is prepared by addition of n-butyllithium (115 mmol, 72 ml of 1.6M in hexane) to dichloromethane (15 ml) in tetrahydrofurane (175 ml) at −78° C. under argon with stirring. To this is added a solution of diisopropoxy methylborane (115 mmol) in diethyl ether (10 ml). After standing for 12 hours the mixture is refluxed for 1 h and then cooled to −78° C. A solution lithiohexamethyldisilazane, prepared by addition of n- butyllithium (115 mmol) to hexamethyldisilazane (128 mmol) in tetrahydrofurane at −78° C., is then added dropwise with stirring. The mixture is then allowed to warm to room temperature and stand for 3 hours. The intermediate diisopropyl [1-[bis(trimethylsilyl)amino]-ethyl]boronate (diisopropyl N-ditrimethylsilyl boroAla) is partially purified by fractional vacuum distillation. Addition to water yields the hydrolysis product (DL)-boroAla.

c. $Ac_2$-(L)-Lys-(DL)-boroAla

Coupling of $Ac_2$-(L)-Lys with (DL)-boroAla can be achieved by the mixed anhydride method of Anderson et al. (J. Am. Chem. Soc. 1967 89:5012–5017). A solution of (DL)-boroAla (5 mmol) and N-methyl morpholine (5 mmol) in DMF (10 ml) is prepared. To a solution of $Ac_2$-(L)-Lys (5 mmol) and N-methylmorpholine (5 mmol) in tetrahydrofuran at −15° C. is added isobutylchloroformate (5 mmol) followed, one minute later, by the (DL)-boroAla solution, also at −15° C. The reaction mixture is allowed to warm to room temperature. The solid is removed by filtration and the solvent removed by evaporation to yield the crude product.

EXAMPLE 2

Resolution of Ac$_2$-(L)-Lys-(DL)-boroAla into
Ac$_2$-(L)-Lys-(L)-boroAla and
Ac$_2$-(L)-Lys-(D)-boroAla The crude material obtained in example 1 can be further purified and resolved into its component diastereomers by HPLC on a C-18 column eluted with a linear gradient of 100% A to 100% B, where A=0.1% TFA in water and B=0.086% TFA in 70% acetonitrile/30% water.

EXAMPLE 3

Nα-Ac-Nε-p-toluenesulfonyl-(L)-Lys-(D)-alaninal
(FIG. 3, B)

a. Nα-Ac-Nε-p-toluenesulfonyl-(L)-Lys

To a vigorously stirred solution of Nα-Ac-(L)-lysine (100 mmol) in 1M NaOH (100 ml) is added p-toluenesulfonyl chloride (140 mmol). Further addition of 1N NaOH is used to maintain the pH above 9 (about 140 ml over the 2hourcourse of the reaction) and an ice bath to keep the reaction at about 20° C. After the alkalai addition is complete the reaction is stirred for 1 hour at room temperature. Unreacted acid chloride is removed by filtration. The reaction mixture is acidified with 5 N HCl to Congo Red and the solvent removed to yield the crude product.

b. Nα-Ac-Nε-p-toluenesulfonyl-(L)-Lys-(D)-alaninol

To a solution of Nα-Ac-Nε-p-toluenesulfonyl-(L)-Lys (5 mmol) and N-methylmorpholine (5 mmol) in tetrahydrofuran at −15° C. is added isobutylchloroformate (5 mmol) followed, one minute later, by (D)-alaninol (5 mmol). The reaction mixture is allowed to warm to room temperature. The solid is removed by filtration and the solvent removed by evaporation to yield the crude product.

b. Nα-Ac-Nε-p-toluenesulfonyl-(L)-Lys-(D)-alaninal

The following procedure is derived from the method described by Thompson (Biochemistry 1973 12:47–51). The crude product from step b is dissolved in chloroform (3 ml) and dimethylsulfoxide (30 mmol). Dicyclohexylcarbodiimide (15 mmol) is added followed by dichloroacetic acid in five aliquotes over 2 hours (7.5 mmol total). Solvent is removed in vacuo and the resulting material dissolved in chloroform, allowed to stand at −20° C., and the dicyclohexylurea removed by filtration. The final product is purified by chromatography on silica gel.

EXAMPLE 4

Nε-(D)-Benzyloxycarbonyl-Nα-(L)-t-butoxycarbonyl-
(D)-methyl ester-meso-2,6
diaminopimelyl-(DL)-trifluoromethylalanine
(FIG. 3, C)

a. Dibenzyloxycarbonyl-meso-2,6-diaminopimelic acid (II) and Dibenzyloxycarbonyl-(DL)-2,6-diaminopimelic acid (III)

Figure 2:
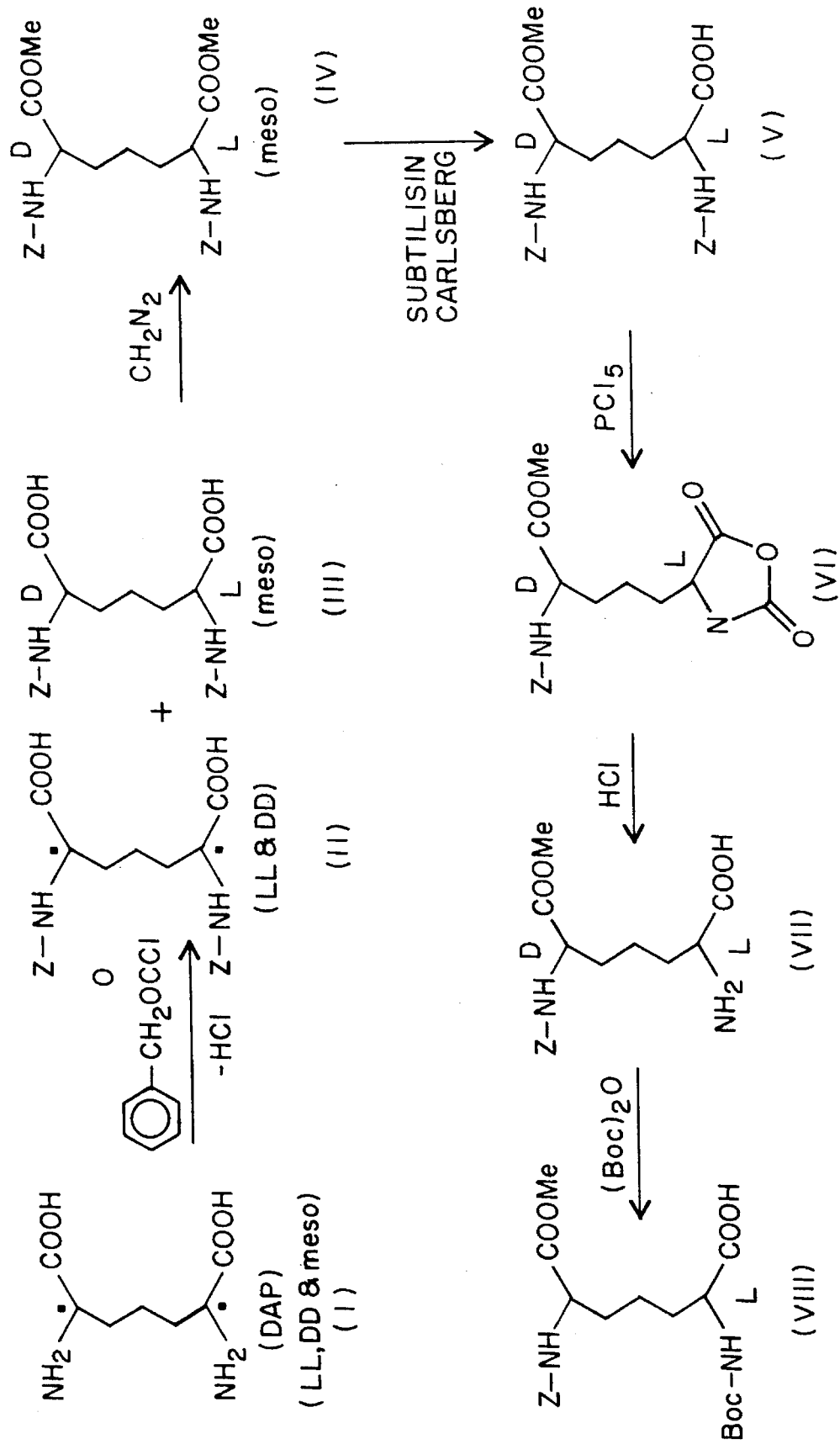
FIG. 2 illustrates the general synthesis scheme for certain steps in the synthesis of N ε-(D)-Benzyloxycarbonyl-Nα-(L)-t-butoxycarbonyl-(D)-methylester-meso-2,6-diaminopimelic acid.

FIG. 2 illustrates the general synthesis scheme for Nε-(D)-Benzyloxycarbonyl-Nα-(L)-t-butoxycarbonyl-(D)-methyl ester-meso-2,6 diaminopimelic acid, using a procedure derived from that of Wade et al. (J. Am. Chem. Soc. 1957 79:648–652). To α,ε-diaminopimelic acid (I) (50 mmol) in 2N NaOH (125 ml) is added carbobenzyloxy chloride (100 mmol), in five portions, with stirring in an ice bath. After the addition of carbobenzyloxy chloride is complete the mixture is stirred for 2 hours at room temperature. Unreacted carbobenzyloxy chloride is removed by ethyl acetate extraction and the aqueous phase acidified to pH 1.7 with 4N HCl. The precipitated oil is taken up in ethyl acetate, dried over sodium sulfate, and concentrated to 50 ml in vacuo. The concentrate is allowed to stand at 4° C. overnight and the precipitate collected by filtration. The precipitate is recrystallized from ethyl acetate to yield (LL) and (DD) dibenzyloxycarbonyl-2,6-diaminopimelic acid (II). The combined ethyl acetate mother liquors from both steps is concentrated, and the residue dissolved in a minimal volume of hot chloroform and allowed to stand for several days to yield the precipitated dibenzyloxycarbonyl-meso-2,6-diaminopimelic acid (III).

b. Dibenzyloxycarbonyl-meso-2,6-diaminopimelic-(D)-methyl ester (V)

The following procedure is derived from that of Kolodziejczyk et al. (Int. J. Peptide Protein Res. 1992 39:382–387). Dibenzyloxycarbonyl-meso-2,6-diaminopimelic acid (10 mmol) (III) is converted to its dimethyl ester with diazomethane, and excess reagent and solvent is removed in vacuo. The crude material is dissolved in 30 ml DMF and to this is added a solution of 0.75 g of Subtilisin Carlsberg from *Bacillus licheniformis* in a 10 ml solution of NaHCO$_3$ (15 mmol) and the mixture stirred overnight at room temp. The solvent is removed in vacuo and the residue dissolved in water (50 ml) and twice extracted with a mixture of ether and benzene (1:4). The aqueous layer is acidified to pH 2 with HCl, extracted with ethyl acetate, and concentrated in vacuo to yield the crude product which can be further purified by chromatography.

c. Nε-(D)-Benzyloxycarbonyl-7-methyl ester-meso-2,6 diaminopimelic acid-Nα-(L)-carboxyanhydride (VI)

The following procedure is derived from that of Kolodziejczyk et al. (Int. J. Peptide Protein Res. 1992 39:382–387). To a solution of (D)-N-benzyloxycarbonyl-(L)-N-carboxyanhydride-meso-2,6-diaminopimelic-(D)-methyl ester (2 mmol) in CH$_2$Cl$_2$ (15 ml) cooled in an ice bath is added PCl$_5$ (2.2 mmol) and the reaction is stirred for 15 min on ice and for 15 min at room temp. The solvent is removed in vacuo and the residue is dissolved in 10 ml benzene and precipitated with 50 ml heptane and kept at 4° C. for 2 h. The product was collected and the procedure repeated to yield the final product.

d. Nε-(D)-Benzyloxycarbonyl-Nα-(L)-t-butoxycarbonyl-(D)-methyl ester-meso-2,6 diaminopimelic acid (VIII)

The following procedure is derived from that of Kolodziejczyk et al. (Int. J. Peptide Protein Res. 1992:39 382–387). To a solution of Nε-(D)-Benzyloxycarbonyl-7-methyl ester-meso-2,6 diaminopimelic acid-Nα-(L)-carboxyanhydride (2.5 mmol) in CH$_3$CN (3 ml) in an ice bath is added 2N HCl (3 ml) and the solution is stirred overnight at room temperature. The solution is dried in vacuo, dissolved in water (20 ml) and extracted with ethyl acetate to remove impurities. The aqueous phase is concentrated and dissolved in water (3 ml) containing K$_2$CO$_3$ (1.2 mmol) and CH$_3$CN (6 ml) and (Boc)$_2$O (1.4 mmol) are added. After 2h at room temperature the product is obtained by extraction with ethyl acetate, acidification to pH 2 with 2N HCl, and reextraction with ethyl acetate. Evaporation of the second ethyl acetate extraction yields the product.

e. 1,1,1-Trifluoro-3-amino-2-butanol hydrochloride

The following procedure is derived from that of Cook et al. (J. Am. Chem. Soc. 1954 76:83–87). To a mixture of trifluoroacetaldehyde ethyl hemiacetal (100 mmol) and K$_2$CO$_3$ is added nitoethane (100 mmol) and the mixture is stirred overnight at 50° C. Brine (25 ml), 1N HCl (15 ml).

The mixture is extracted with diethyl ether (2×100 ml) and the combined organic phases pooled, dried over $Na_2SO_4$, and concentrated by evaporation. The residue is purified by chromatography on silica gel. This material is dissolved in 50 ml of absolute ethanol and reduced under hydrogen (40 lb) in the presence of Raney nickel (3 g). After 4 hours concentrated HCl is added (10 ml), most of the solvent removed by rotary evaporation, and the product collected by filtration.

f. Nε-(D)-Benzyloxycarbonyl-Nα-(L)-t-butoxycarbonyl-(D)-methyl ester-meso-2,6 diaminopimethyl-N-1,1,1-trifluoro-3-amino-2-butanol To a solution of Nε-(D)-Benzyloxycarbonyl-Nα-(L)-t-butoxycarbonyl-(D)-methyl ester-meso-2,6 diaminopimelic acid (10 mmol), and N-methylmorpholine (10 mmol) in THF (100 ml) at −15° C. is added isobutyl chlorocarbonate (10 mmol) followed 5 min later by a solution of 1,1,1-Trifluoro-3-amino-2-butanol hydrochloride (10 mmol) and N-methylmorpholine (10 mmol) in THF (20 ml) at −15° C., and the reaction allowed to proceed at room temperature for 30 min. The N-methylmorpholine HCl is removed by filtration and the product obtained by the removal of solvent in vacuo.

g. Nε-(D)-Benzyloxycarbonyl-Nα-(L)-t-butoxycarbonyl-(D)-methyl ester-meso-2,6 diaminopimelyl-(DL)-trifluoromethylalanine (FIG. 3, C)

The following procedure is derived from that of Imperiali et al. (Tett. Lett. 1986 27:135–138). To a solution of Nε-(D)-Benzyloxycarbonyl-Nα-(L)-t-butoxycarbonyl-(D)-methyl ester-meso-2,6 diaminopimelyl-N-1,1,1-trifluoro-3- amino-2-butanol (10 mmol) in 0.3N NaOH (100 ml) is added $KMnO_4$ (12 mmol) and the mixture stirred for 0.5 hours at 25° C. The pH is adjusted to 4 with 1N HCl and the product is extracted with ethyl acetate, concentrate in vacuo, and purified by chromatography on silica gel.

EXAMPLE 5

Nα-Boc-Nε-benzyloxycarbonyl-(L)-Lys-(D)-Ala-$CH_2Cl$ (FIG. 3, E)

a. HCl (D)-Ala-$CH_2Cl$

The following procedure is a modification of that given by Powers (Meth. Enzymol. 1976 46:197–208). To a solution of Boc-(D)-Ala (10 mmol) in THF (20 ml) at −10° C. is added N-methylmorpholine (10 mmol) followed by isobutylchloroformate (10 mmol). The solution is then cold filtered to remove precipitated N-methylmorpholine HCl and added to cold ethereal diazomethane (30 mmol). The mixture is stirred overnight at room temperature. Dry HCl is bubbled through the solution until the solution turns colorless, and the product HCl (D)-Ala-$CH_2Cl$ is isolated by removal of solvent in vacuo.

b. Nα-Boc-Nε-benzyloxycarbonyl-(L)-Lys-(D)-Ala-$CH_2Cl$

To a solution of Nα-Boc-Nε-benzyloxycarbonyl-(L)-Lys-N-hydroxysuccinimide ester (7.5 mmol) and $NaHCO_3$ (7.5 mmol) in 20 ml water is added HCl (D)-Ala-$CH_2Cl$ (10 mmol). The solution is stirred overnight at room temperature. The pH of the solution is adjusted to 7.0 with 1N HCl and the solution is extracted with ethyl acetate. The product is recovered from the ethyl acetate extract by solvent removal in vacuo.

EXAMPLE 6

N-Benzoyl-(DL)-Ala-$CH_2F$ (FIG. 3, D)

The following procedure is that given by Rasnick (Anal. Biochem. 1985 149:461–465). Fluoroacetic anhydride is prepared from fluoroacetic acid and dicyclohexylcarbodiimide (0.5 equivalents) in dichloromethane and purified by distillation. To a mixture of N-Benzoyl-(DL)-alanine (40 mmol) and fluoroacetic anhydride (80 mmol) in 10 ml benzene on an ice bath is added triethylamine (80 mmol) and then 4-dimethylaminopyridine (2 mmol). The solution is stirred for two hours at room temperature, the solvent removed, and the product purified by chromatography on silica gel.

EXAMPLE 7

$Ac_2$-(L)-Lys-(DL)-boroPro (FIG. 3, F)

a. Boc-pyrrole

The following method is that described by Grehn and Ragnarsson (1984 23:296–297). 4-Dimethylaminopyridine (10 mmol) and $Boc_2O$ (120 mmol) are added to a stirred mixture of pyrrole (100 mmol) in dry $CH_3CN$ (200 ml) at room temperature. After 24 hr the excess $Boc_2O$ is destroyed by addition of 2-diethylaminoethylamine (20 mmol) the product is isolated by addition of either (1000 ml), extraction of the ether phase with 1M $KHSO_4$ (4×500 ml), water (1×500 ml), 1M $NaHCO_3$, and brine (1×500 ml), and the ether phase dried over $MgSO_4$. After removal of solvent the product is purified by distillation.

b. Boc-pyrrole-2-boric acid

The following method is that described by Kelly et al. (1933 49:1009–1016). To a solution of teramethylpiperidinc (52 mmol) in THF (275 mL) at 78° C. under argon is added a 2M solution of butyllithium in hexanes (52 mmol). After 15 min Boc-pyrrole (52 mmol) in THF (10 ml) is added and the solution stirred for 4 hr at 78° C. Triethylborate (176 mmol) is then added and the mixture allowed to warm to room temperature over 3 hr. After an additional 12 hr the reaction mixture is diluted with ether (500 ml) and washed with 1M $KHSO_4$ (3×100 ml) and 1M $NaHCO_3$. The either layer is dried over $MgSO_4$, the solvent removed by rotary evaporation, and the product purified by chromatography on silica gel.

c. (DL)-boroPro

The following method is that described by Kelly et al. (1993 49:1009–1016). A solution of Boc-pyrrole-2-boric acid (24 mmol) in EtOAc (100 ml) is hydrogenated over 5% Pt (500 mg) at 50 psi for 4 hr. The product Boc-boroPro is purified by chromatography on silica gel. A solution of Boc-boroPro (20 mmol) is treated with 3M HCl in dry EtOAc for 2 hr. The crude material is obtained by removal of solvent by rotary evaporation.

d. $Ac_2$-(L)-Lys-(DL)-boroPro

Coupling of $Ac_2$-(L)-Lys with (DL)-boroPro can be achieved by the mixed anhydride method of Anderson et al. (J. Am. Chem. Soc. 1967 89:5012–5017). A solution of (DL)-boroPro (5 mmol) and N-methyl morpholine (5 mmol) in DMF (10 ml) is prepared. To a solution of $Ac_2$-(L)-Lys (5 mmol) and N-methylmorpholine (5 mmol) in tetrahydrofuran at −15° C. is added isobutylchloroformate (5 mmol) followed, one minute later, by the (DL)-boroAla solution, also at −15° C. The reaction mixture is allowed to warm to room temperature. The solid is removed by filtration and the solvent removed by evaporation to yield the crude product.

EXAMPLE 8

Ac$_2$-(L)-Lys-aminocylopentane carboxaldehyde
(FIG. 3, G)

a. Ac$_2$-(L)-Lys-aminocylopropanemethanol

To a solution of Ac$_2$-(L)-Lys (5 mmol) (EXAMPLE 1a) and N-methylmorpholine (5 mmol) in tetrahydrofuran at −15° C. is added isobutylchloroformate (5 mmol) followed, one minute later, by aminocylopropanemethanol (5 mmol). The reaction mixture is allowed to warm to room temperature. The solid is removed by filtration and the solvent removed by evaporation to yield the crude product.

b. Ac$_2$-(L)-Lys-aminocylopentane carboxaldehyde

The following procedure is derived from the method described by Thompson (Biochemistry 1973 12:47–51). The crude product from step b was dissolved in chloroform (3 ml) and dimethylsulfoxide (30 mmol). Dicyclohexylcarbodiimide (15 mmol) was added followed by dichloroacetic acid in five aliquots over 2 hours (7.5 mmol total). Solvent was removed in vacuo and the resulting material dissolved in chloroform, allowed to stand at −20° C., and the dicyclohexylurea removed by filtration. The final product was purified by chromatography on silica gel.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a bacterial infection in an animal, which method comprises administering to said animal an antibacterial amount of a compound sufficient to to inhibit bacterial cell wall biosynthesis by a penicillin binding protein of bacteria causing the infection, the compound represented by the general formula

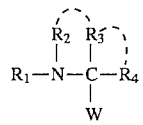

wherein

W represents $BY_1Y_2$, or $C(=O)R_5$;

$R_1$ represents a C-terminally linked amino acid residue or amino acid analog, or a C-terminally linked peptide or peptide analog, or

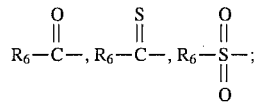

$R_2$ represents hydrogen, an alkyl, an alkenyl, an alkynyl, —(CH$_2$)m-R$_7$, —(CH$_2$)m-OH, —(CH$_2$)m-O-alkyl, —(CH$_2$)m-O-alkenyl, —(CH$_2$)m-O-alkynyl, —(CH$_2$)m-O-C(=O)-alkyl, —(CH$_2$)m-O-C(=O)-alkenyl, —(CH$_2$)m-O-C(=O)-alkynyl —(CH$_2$)m-O-C(=O)-(CH$_2$)m-R$_7$;

$R_3$ and $R_4$ each represent hydrogen, a alkyl, a alkenyl, a alkynyl, —(CH$_2$)m-R$_7$, —(CH$_2$)n-OH, —(CH$_2$)n-O-alkyl, —(CH$_2$)n-O-alkenyl, —(CH$_2$)n-O-alkynyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, an α-carbon linked side chain of an amino acid or an amino acid analog,

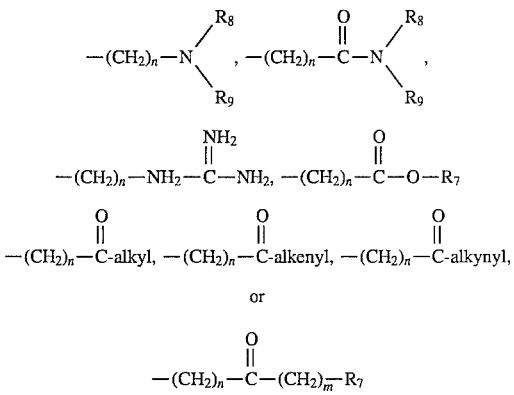

$R_2$ and $R_3$ taken together can complete a ring having from 4 to 8 atoms in the ring structure, or, provided $R_2$ and $R_3$ are not taken together forming a ring, $R_3$ and $R_4$ taken together can complete a ring having from 3 to 8 atoms in the ring structure, $Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure, $R_5$ represents H, an alkyl, an alkenyl, an alkynyl, —(CH$_2$)m-R$_7$, —(CH$_2$)n-OH, —CH$_2$)n-O-alkyl, —(CH$_2$)n-O-alkenyl, —(CH$_2$)n-O-alkynyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, —CH$_2$O-R$_{10}$, $R_6$ represents hydrogen, a halogen, a alkyl, a alkenyl, a alkynyl, an aryl, —(CH$_2$)$_m$-R$_7$, —(CH$_2$)$_m$-OH, —(CH$_2$)$_m$-O-alkyl, —(CH$_2$)$_m$-O-alkenyl, —(CH$_2$)$_m$-O-alkynyl, —(CH$_2$)$_m$-O-(CH$_2$)$_m$-R$_7$, —(CH$_2$)$_m$SH, —(CH$_2$)$_m$-S-alkyl, —(CH$_2$)$_m$-S-alkenyl, —(CH$_2$)$_m$S-alkynyl, —(CH$_2$)$_m$-S-(CH$_2$)$_m$-R$_7$,

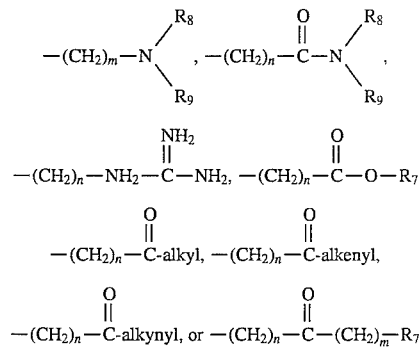

$R_7$ represents an aryl, a cycloalkyl, a cycloalkenyl, or a heterocycle;

$R_8$ and $R_9$ each independently represent hydrogen, alkyl, alkenyl, —(CH$_2$)$_m$-R$_7$, —C(=O)-alkyl, —C(=O)-alkenyl, —C(=O)-alkynyl, —C(=O)-(CH$_2$)m-R$_7$, or $R_8$ and $R_9$ taken together with the N atom to which they are attached complete a heterocyclic ring having from 4 to 8 atoms in the ring structure;

$R_{10}$ represents represents a C-terminally linked amino acid residue or amino acid analog, or a C-terminally linked peptide or peptide analog,

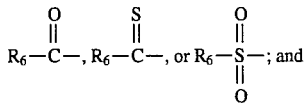

m is zero or an integer in the range of 1 to 8; and n is an integer in the range of 1 to 8.

2. The method of claim 1, wherein the compound is introduced into the body by injection.

3. The method according to claim 2, wherein the method of injection is selected from the group consisting of subcutaneous, intramuscular, intraperitoneal and intravenous injection.

4. The method of claim 1, wherein the compound is introduced by a method selected from the group consisting of aerosol inhalation, transdermal or transbuccal absorption and rectal suppository.

5. The method of claim 1, wherein W is repesented by the formula

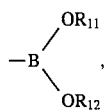

wherein $R_{11}$ and $R_{12}$ each independently represent hydrogen, a alkyl, or a pharmaceutically acceptable salt, or $R_{11}$ and $R_{12}$ taken together with the O-B-O atoms to which they are attached complete a heterocyclic ring having from 5 to 8 atoms in the ring structure.

6. The method of claim 1, wherein W is represented by the formula

wherein $R_{13}$ is a hydrogen or

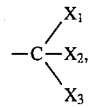

and $X_1$, $X_2$ and $X_3$ each represent a hydrogen or a halogen.

7. The method of claim 1, wherein $R_3$ is a methyl and $R_4$ is a hydrogen, and the carbon to which $R_3$ and $R_4$ are bonded is a (D)-isomer.

8. The method of claim 1, wherein the bacterial infection is selected from the group consisting of a Staphylococcus infection, a Streptococcus infection, an Enterobacteriaceae infection, and Enterococcus infection, a Mycobacterium infection, a Neisseria infection, a Pseudomonas infection, a Shigella infection, an Escherichia infection, a Bacillus infection, a Micrococcus infection, an Arthrobacter infection, and a Peptostreptococcus infection.

9. A method of killing bacterial microorganisms dependent on a cell wall biosynthesis activity of a penicillin binding protein for viability, comprising contacting the microorganisms with an effective dosage of a penicillin binding protein inhibitor represented by the general formula

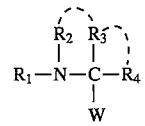

wherein

W represents $BY_1Y_2$, or $C(=O)R_5$ $R_1$ represents a C-terminally linked amino acid residue or amino acid analog, or a C-terminally linked peptide or peptide analog, or

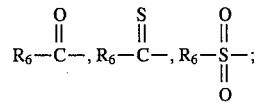

$R_2$ represents hydrogen, an alkyl, an alkenyl, an alkynyl, —$(CH_2)$m-$R_7$, —$(CH_2)$m-OH, —$(CH_2)$m-O-alkyl, —$(CH_2)$m-O-alkenyl, —$(CH_2)$m-O-alkynyl, —$(CH_2)$m-O-C(=O)-alkyl, —$(CH_2)$m-O-C(=O)-alkenyl, —$(CH_2)$m-O-C(=O)-alkynyl, —$(CH_2)$m-O-C$(CH_2)$m-$R_7$;

$R_3$ and $R_4$ each represent hydrogen, a alkyl, a alkenyl, a alkynyl, —$(CH_2)$m-$R_7$, —$(CH_2)$n-OH, —$(CH_2)$n-O-alkyl, —$(CH_2)$n-O-alkenyl, —$(CH_2)$n-O-alkynyl, —$(CH_2)$n-O-$(CH_2)$m-$R_7$, —$(CH_2)$n-SH, —$(CH_2)$n-S-alkyl, —$(CH_2)$n-S-alkenyl, —$(CH_2)$n-S-alkynyl, —$(CH_2)$m-$R_7$, an α-carbon linked side chain of an amino acid or an amino acid analog,

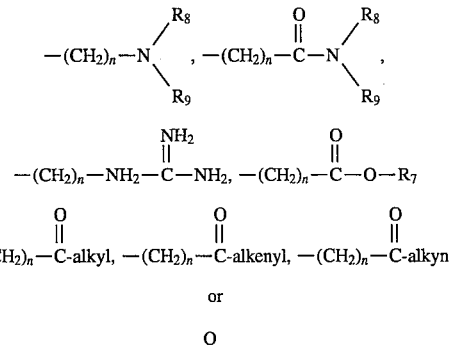

$R_2$ and $R_3$ taken together can complete a ring having from 4 to 8 atoms in the ring structure, or, provided $R_2$ and $R_3$ are not taken together forming a ring, $R_3$ and $R_4$ taken together can complete a ring having from 3 to 8 atoms in the ring structure, $Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure, $R_5$ represents H, an alkyl, an alkenyl, an alkynyl, —$(CH_2)$m-$R_7$, —$(CH_2)$n-OH, —$(CH_2)$n-O-alkyl, —$(CH_2)$n-O-alkenyl, —$(CH_2)$n-O-alkynyl, —$(CH_2)$n-O-$(CH_2)$m-$R_7$, —$(CH_2)$n-SH, —$(CH_2)$n-S-alkyl, —$(CH_2)$n-S-alkenyl, —$(CH_2)$n-S-alkynyl, —$(CH_2)$n-S-$(CH_2)$m-$R_7$, —$CH_2O$-$R_{10}$, $R_6$ represents hydrogen, a halogen, a alkyl, a alkenyl, a alkynyl, an aryl, —$(CH_2)$m-$R_7$, —$(CH_2)_m$-OH, —$(CH_2)_m$-O-alkyl, —$(CH_2)_m$-O-alkenyl, —$(CH_2)_m$-

O-alkynyl, —(CH$_2$)$_m$-O-(CH$_2$)$_m$-R$_7$, —(CH$_2$)$_m$-SH, —(CH$_2$)$_m$-S-alkyl, —(CH$_2$)$_m$-S-alkenyl, —(CH$_2$)$_m$-S-alkynyl, —(CH$_2$)$_m$-S-(CH$_2$)$_m$-R$_7$,

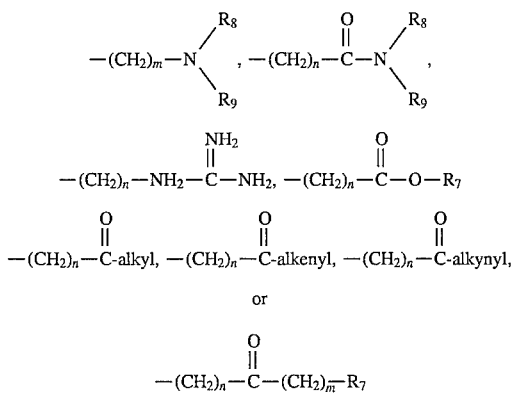

R$_7$ represents an aryl, a cycloalkyl, a cycloalkenyl, or a heterocycle;

R$_8$ and R$_9$ each independently represent hydrogen, alkyl, alkenyl, —(CH$_2$)$_m$-R$_7$, C(=O)-alkyl, —C(=O)-alkenyl, —C(=O)-alkynyl, —C(=O)-(CH$_2$)$_m$-R$_7$, or R$_8$ and R$_9$ taken together with the N atom to which they are attached complete a heterocyclic ring having from 4 to 8 atoms in the ring structure;

R$_{10}$ represents represents a C-terminally linked amino acid residue or amino acid analog, or a C-terminally linked peptide or peptide analog,

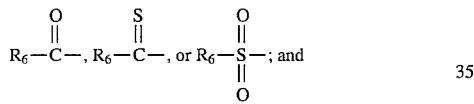

m is zero or an integer in the range of 1 to 8; and n is an integer in the range of 1 to 8.

10. The method of claim 9, wherein the compound inhibits enzymatic bacterial cell wall biosynthesis by a penicillin binding protein.

11. The method of claim 9, which method is used to inhibit bacterial growth on non-living matter.

12. A pharmaceutical composition comprising, in a pharmaceutically-acceptable carrier, an antibacterial amount of a compound represented by the general formula

wherein

W represents BY$_1$Y$_2$, or C(=O)R$_5$

R$_1$ represents a C-terminally linked amino acid residue or amino acid analog, or a C-terminally linked peptide or peptide analog, or

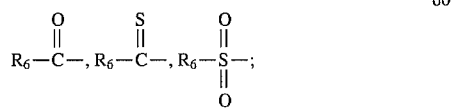

R$_2$ represents hydrogen, an alkyl, an alkenyl, an alkynyl, —(CH$_2$)m-R$_7$, —(CH$_2$)m-OH, —(CH$_2$)m-O-alkyl, —(CH$_2$)m-O-alkenyl, —(CH$_2$)m-O-alkynyl, —(CH$_2$)m-O-C(=O)-alkyl, -(CH$_2$)m-O-C(=O)-alkenyl, —(CH$_2$)m-O-C(=O)-alkynyl —(CH$_2$)m-O-C(=O)-(CH$_2$)m-R$_7$;

R$_3$ and R$_4$ each represent hydrogen, a alkyl, a alkenyl, a alkynyl, —(CH$_2$)m-R$_7$, —(CH$_2$)n-OH, —(CH$_2$)n-O-alkyl, —(CH$_2$)n-O-alkenyl, —(CH$_2$)n-O-alkynyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, an α-carbon linked side chain of an amino acid or an amino acid analog,

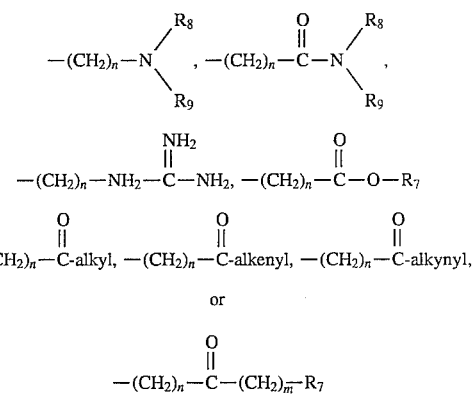

R$_2$ and R$_3$ taken together can complete a ring having from 4 to 8 atoms in the ring structure, or, provided R$_2$ and R$_3$ are not taken together forming a ring, R$_3$ and R$_4$ taken together can complete a ring having from 3 to 8 atoms in the ring structure, Y$_1$ and Y$_2$ can independently or together be OH, or a group capable of being hydrolyzed to a hydroxyl group, including cyclic derivatives where Y$_1$ and Y$_2$ are connected via a ring having from 5 to 8 atoms in the ring structure, R$_5$ represents H, an alkyl, an alkenyl, an alkynyl, —(CH$_2$)m-R$_7$, —(CH$_2$)n-OH, -(CH$_2$)n-O-alkyl, —(CH$_2$)n-O-alkenyl, —(CH$_2$)n-O-alkynyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, —CH$_2$O-R$_{10}$, R$_6$ represents hydrogen, a halogen, a alkyl, a alkenyl, a alkynyl, an aryl, —(CH$_2$)$_m$-R$_7$, —(CH$_2$)$_m$-OH, —(CH$_2$)$_m$-O-alkyl, —(CH$_2$)$_m$-O-alkenyl, —(CH$_2$)$_m$-O-alkynyl, —(CH$_2$)$_m$-O-(CH$_2$)$_m$-R$_7$, —(CH$_2$)$_m$-SH, —(CH$_2$)$_m$-S-alkyl, —(CH$_2$)$_m$-S-alkenyl, —(CH$_2$)$_m$-S-alkynyl, —(CH$_2$)$_m$-S-(CH$_2$)$_m$-R$_7$,

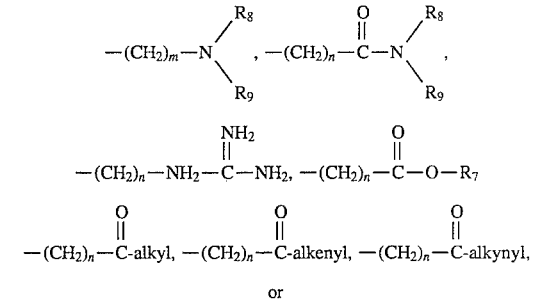

-continued

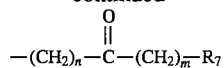

R$_7$ represents an aryl, a cycloalkyl, a cycloalkenyl, or a heterocycle;

R$_8$ and R$_9$ each independently represent hydrogen, alkyl, alkenyl, —(CH$_2$)$_m$-R$_7$, —C(=O)-alkyl, —C(=O)-alkenyl, —C(=O)-alkynyl, —C(=O)-(CH$_2$)$_m$-R$_7$, or R$_8$ and R$_9$ taken together with the N atom to which they are attached complete a heterocyclic ring having from 4 to 8 atoms in the ring structure;

R$_{10}$ represents represents a C-terminally linked amino acid residue or amino acid analog, or a C-terminally linked peptide or peptide analog,

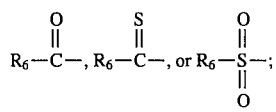

m is zero or an integer in the range of 1 to 8; and n is an integer in the range of 1 to 8.

13. The pharmaceutical composition of claim 12, comprising a purified or partially purified enantiomer or diastereomer of said antibacterial compound.

14. The pharmaceutical composition of claim 12, wherein said antibacterial compound is present in said composition in combination with other antibacterial agents.

15. A feedstock comprising an antibacterial amount of a compound represented by the general formula

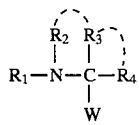

wherein

W represents BY$_1$Y$_2$, or C(=O)R$_5$

R$_1$ represents a C-terminally linked amino acid residue or amino acid analog, or a C-terminally linked peptide or peptide analog, or

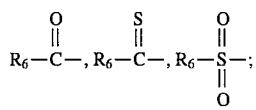

R$_2$ represents hydrogen, an alkyl, an alkenyl, an alkynyl, —(CH$_2$)m-R$_7$, —(CH$_2$)m-OH, —(CH$_2$)m-O-alkyl, —(CH$_2$)m-O-alkenyl, —(CH$_2$)m-O-alkynyl, —(CH$_2$)m-O-C(=O)-alkyl, —(CH$_2$)m-O-C(=O)-alkenyl, —(CH$_2$)m-O-C(=O)-alkynyl —(CH$_2$)m-O-C(=O)-(CH$_2$)m-R$_7$;

R$_3$ and R$_4$ each represent hydrogen, a alkyl, a alkenyl, a alkynyl, —(CH$_2$)m-R$_7$, —(CH$_2$)n-OH, —(CH$_2$)n-O-alkyl, —(CH$_2$)n-O-alkenyl, —(CH$_2$)n-O-alkynyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, an α-carbon linked side chain of an amino acid or an amino acid analog,

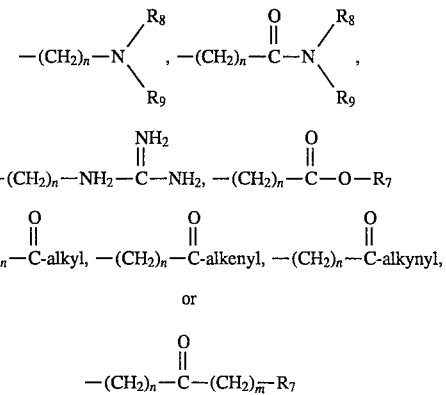

R$_2$ and R$_3$ taken together can complete a ring having from 4 to 8 atoms in the ring structure, or, provided R$_2$ and R$_3$ are not taken together forming a ring, R$_3$ and R$_4$ taken together can complete a ring having from 3 to 8 atoms in the ring structure, Y$_1$ and Y$_2$ can independently or together be OH, or a group capable of being hydrolyzed to a hydroxyl group, including cyclic derivatives where Y$_1$ and Y$_2$ are connected via a ring having from 5 to 8 atoms in the ring structure, R$_5$ represents H, an alkyl, an alkenyl, an alkynyl, —(CH$_2$)m-R$_7$, —(CH$_2$)n-OH, —(CH$_2$)n-O-alkyl, —(CH$_2$)n-O-alkenyl, —(CH$_2$)n-O-alkynyl, —(CH$_2$)n-O-(CH$_2$)m-R$_7$, —(CH$_2$)n-SH, —(CH$_2$)n-S-alkyl, —(CH$_2$)n-S-alkenyl, —(CH$_2$)n-S-alkynyl, —(CH$_2$)n-S-(CH$_2$)m-R$_7$, —CH$_2$O-R$_{10}$, R$_6$ represents hydrogen, a halogen, a alkyl, a alkenyl, a alkynyl, an aryl, —(CH$_2$)$_m$-R$_7$, —(CH$_2$)$_m$-OH, —(CH$_2$)$_m$-O-alkyl, —(CH$_2$)$_m$-O-alkenyl, —(CH$_2$)$_m$-O-alkynyl, —(CH$_2$)$_m$O-(CH$_2$)$_m$-R$_7$, —(CH$_2$)$_m$-SH, —(CH$_2$)$_m$-S-alkyl, —(CH$_2$)$_m$-S-alkenyl, —(CH$_2$)$_m$-S-alkynyl, —(CH$_2$)$_m$-S-(CH$_2$)$_m$-R$_7$,

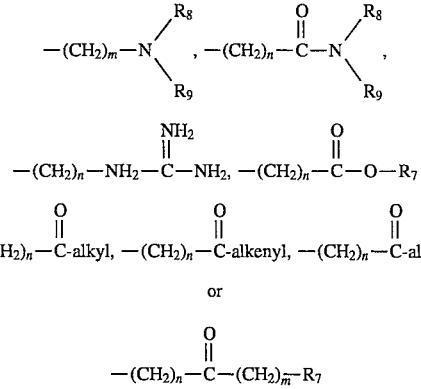

R$_7$ represents an aryl, a cycloalkyl, a cycloalkenyl, or a heterocycle;

R$_8$ and R$_9$ each independently represent hydrogen, alkyl, alkenyl, —(CH$_2$)$_m$-R$_7$, —C(=O)-alkyl, —C(=O)-alkenyl, —C(=O)-alkynyl, —C(=O)-(CH$_2$)$_m$-R$_7$, or R$_8$ and R$_9$ taken together with the N atom to which they are attached complete a heterocyclic ring having from 4 to 8 atoms in the ring structure;

R$_{10}$ represents represents a C-terminally linked amino acid residue or amino acid analog, or a C-terminally linked peptide or peptide analog, 5,574,017

31

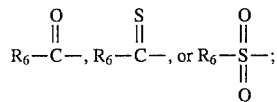

m is zero or an integer in the range of 1 to 8; and n is an integer in the range of 1 to 8.

16. The method of claim 1, wherein the compound is represented by the general formula:

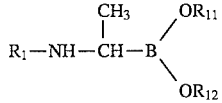

wherein $R_1$ represents a C-terminally linked amino acid residue or amino acid analog, or a C-terminally linked peptide or peptide analog, or

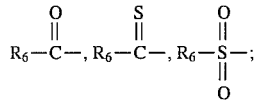

$R_6$ represents hydrogen, a halogen, a alkyl, a alkenyl, a alkynyl, an aryl, —$(CH_2)_m$-$R_7$, —$(CH_2)_m$-OH, —$(CH_2)_m$-O-alkyl, —$(CH_2)_m$-O-alkenyl, —$(CH_2)_m$-O-alkynyl, —$(CH_2)_m$-O-$(CH_2)_m$-$R_7$, —$(CH_2)_m$-SH, —$(CH_2)$m-S-alkyl, —$(CH_2)$m-S-alkenyl, —$(CH_2)_m$-S-alkynyl, —$(CH_2)_m$-S-$(CH_2)_m$-$R_7$,

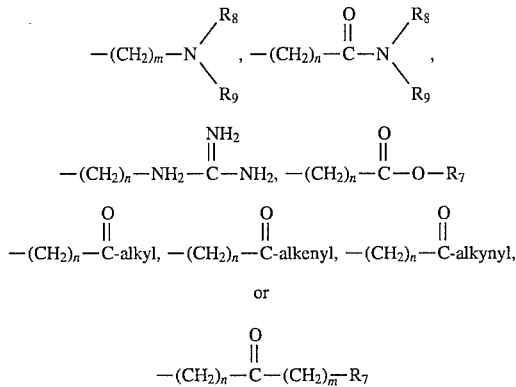

$R_7$ represents an aryl, a cycloalkyl, a cycloalkenyl, or a heterocycle;

$R_8$ and $R_9$ each independently represent hydrogen, alkyl, alkenyl, —$(CH_2)_m$-$R_7$, —C(=O)-alkyl, —C(=O)-alkenyl, —C(=O)-alkynyl, —C(=O)-$(CH_2)_m$-$R_7$, or $R_8$ and $R_9$ taken together with the N atom to which they are attached complete a heterocyclic ring having from 4 to 8 atoms in the ring structure;

$R_{11}$ and $R_{12}$ each independently represent hydrogen, a alkyl, or a pharmaceutically acceptable salt, or $R_{11}$ and $R_{12}$ taken together with the O-B-O atoms to which they are attached complete a heterocyclic ring having from 5 to 8 atoms in the ring structure;

m is zero or an integer in the range of 1 to 8; and n is an integer in the range of 1 to 8.

17. The method of claim 1, wherein the compound is represented by the general formula:

32

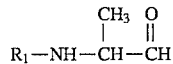

wherein $R_1$ represents a C-terminally linked amino acid residue or amino acid analog, or a C-terminally linked peptide or peptide analog, or

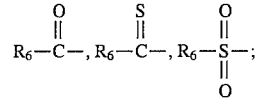

$R_6$ represents hydrogen, a halogen, a alkyl, a alkenyl, a alkynyl, an aryl, —$(CH_2)_m$-$R_7$, —$(CH_2)_m$-OH, —$(CH_2)_m$-O-alkyl, —$(CH_2)_m$-O-alkenyl, —$(CH_2)_m$-O-alkynyl, —$(CH_2)_m$-O-$(CH_2)_m$-$R_7$, —$(CH_2)_m$-SH, —$(CH_2)_m$-S-alkyl, —$(CH_2)_m$-S-alkenyl, —$(CH_2)_m$-S-alkynyl, $(CH_2)_m$-S-$(CH_2)_m$-$R_7$,

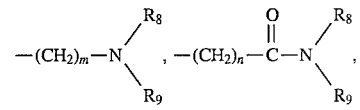

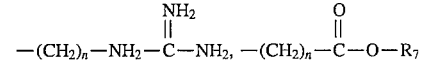

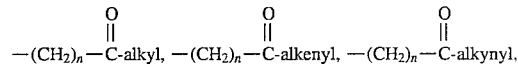

or

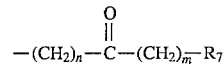

$R_7$ represents an aryl, a cycloalkyl, a cycloalkenyl, or a heterocycle;

$R_8$ and $R_9$ each independently represent hydrogen, alkyl, alkenyl, —$(CH_2)_m$-$R_7$, —C(=O)-alkyl, —C(=O)-alkenyl, —C(=O)-alkynyl, —C(=O)-$(CH_2)_m$-$R_7$, or $R_8$ and $R_9$ taken together with the N atom to which they are attached complete a heterocyclic ring having from 4 to 8 atoms in the ring structure; and m is zero or an integer in the range of 1 to 8; and n is an integer in the range of 1 to 8.

18. The method of claim 1, wherein the compound is represented by the general formula:

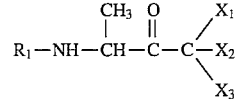

wherein $R_1$ represents a C-terminally linked amino acid residue or amino acid analog, or a C-terminally linked peptide or peptide analog, or

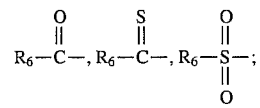

$R_6$ represents hydrogen, a halogen, a alkyl, a alkenyl, a alkynyl, an aryl, —$(CH_2)_m$-$R_7$, —$(CH_2)_m$-OH, —$(CH_2)_m$-O-alkyl, —$(CH_2)_m$-O-alkenyl, —$(CH_2)_m$-O-alkynyl, —$(CH_2)_m$-O-$(CH_2)_m$-$R_7$, —$(CH_2)_m$-SH, —$(CH_2)_m$-S-alkyl, —$(CH_2)_m$-S-alkenyl, —$(CH_2)_m$-S-alkynyl, —$(CH_2)_m$-S-$(CH_2)_m$-$R_7$,

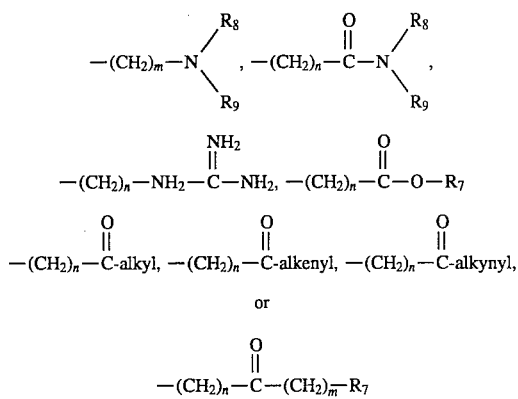

$R_7$ represents an aryl, a cycloalkyl, a cycloalkenyl, or a heterocycle;

$R_8$ and $R_9$ each independently represent hydrogen, alkyl, alkenyl, —$(CH_2)_m$-$R_7$, —C(=O)-alkyl, —C(=O)-alkenyl, —C(=O)-alkynyl, —C(=O)-$(CH_2)_m$-$R_7$, or $R_8$ and $R_9$ taken together with the N atom to which they are attached complete a heterocyclic ring having from 4 to 8 atoms in the ring structure;

$X_1$, $X_2$ and $X_3$ each represent a hydrogen or a halogen; and m is zero or an integer in the range of 1 to 8; and n is an integer in the range of 1 to 8.

19. The method of claim 10, wherein the bacterial infection is selected from the group consisting of a Staphylococcus infection, a Streptococcus infection, an Enterobacteriaceae infection, and Enterococcus infection, a Mycobacterium infection, a Neisseria infection, a Pseudomonas infection, a Shigella infection, an Escherichia infection, a Bacillus infection, a Micrococcus infection, an Arthrobacter infection, and a Peptostreptococcus infection.

20. The method of claim 17, wherein the bacterial infection is selected from the group consisting of a Staphylococcus infection, a Streptococcus infection, an Enterobacteriaceae infection, and Enterococcus infection, a Mycobacterium infection, a Neisseria infection, a Pseudomonas infection, a Shigella infection, an Escherichia infection, a Bacillus infection, a Micrococcus infection, an Arthrobacter infection, and a Peptostreptococcus infection.

21. The method of claim 18, wherein the bacterial infection is selected from the group consisting of a Staphylococcus infection, a Streptococcus infection, an Enterobacteriaceae infection, and Enterococcus infection, a Mycobacterium infection, a Neisseria infection, a Pseudomonas infection, a Shigella infection, an Escherichia infection, a Bacillus infection, a Micrococcus infection, an Arthrobacter infection, and a Peptostreptococcus infection.

* * * * *